United States Patent
Williams (10) Patent No.: US 10,624,637 B2
(45) Date of Patent: **\*Apr. 21, 2020**

(54) COUPLING MEMBER CONFIGURED FOR USE WITH SURGICAL DEVICES

(71) Applicant: Covidien LP, Mansfield, MA (US)

(72) Inventor: Justin Williams, Southbury, CT (US)

(73) Assignee: Covidien LP, Mansfield, MA (US)

( \* ) Notice: Subject to any disclaimer, the term of this patent is extended or adjusted under 35 U.S.C. 154(b) by 318 days.

This patent is subject to a terminal disclaimer.

(21) Appl. No.: 15/690,585

(22) Filed: Aug. 30, 2017

(65) Prior Publication Data

US 2017/0360440 A1 Dec. 21, 2017

Related U.S. Application Data

(63) Continuation of application No. 13/936,289, filed on Jul. 8, 2013, now Pat. No. 9,757,129.

(51) Int. Cl.
*A61B 17/072* (2006.01)
*A61B 17/00* (2006.01)
(Continued)

(52) U.S. Cl.
CPC ............ *A61B 17/07207* (2013.01); *A61B 2017/0046* (2013.01); *A61B 2017/00473* (2013.01); *F16B 7/042* (2013.01); *F16D 1/108* (2013.01)

(58) Field of Classification Search
CPC ............ A61B 1/00121; A61B 1/00112; A61B 2562/225; A61B 17/07207;
(Continued)

(56) References Cited

U.S. PATENT DOCUMENTS 2,291,593 A * 7/1942 Hubbard .................. B25G 1/04
                                                            294/174
2,319,992 A * 5/1943 Hubbard .................. B25G 1/04
                                                            294/174
(Continued)

FOREIGN PATENT DOCUMENTS

EP 0634144 A1 1/1995
EP 1690502 A1 8/2006
(Continued)

OTHER PUBLICATIONS

Chinese Office Action dated Aug. 3, 2017, issued in Chinese Appln. No. 2014103234650.
(Continued)

*Primary Examiner* — Nathaniel C Chukwurah
*Assistant Examiner* — Lucas E. A. Palmer
(74) *Attorney, Agent, or Firm* — Carter, DeLuca & Farrell LLP (57) ABSTRACT

A surgical apparatus is provided. The surgical apparatus includes a surgical actuating device including a shaft having supporting a first coupling member. The first coupling member includes one or more pairs of apertures. The reload includes a second coupling member including a locking assembly. The second coupling member includes a pair of spring pins positionable within the pair of apertures. The spring pins being movable from an inward position to a radial outward position. The locking assembly includes a lock plate that is moveable from a first position located between the spring pins to a second position spaced from the spring pins. In the radial outward position, the spring pins are received within the apertures of the first coupling member to secure the reload to the surgical actuating member and when the lock plate is in the first position, the reload cannot be separated from the surgical actuating device.

10 Claims, 7 Drawing Sheets

(51) Int. Cl.
*F16B 7/04* (2006.01)
*F16D 1/108* (2006.01)

(58) Field of Classification Search
CPC ...... A61B 2018/00172; A61B 17/0783; A61B 2017/07214; A61B 2017/07271; A61B 17/068; B25F 3/00
USPC .................. 403/109.3; 227/175.1, 175.4
See application file for complete search history.

(56) References Cited

U.S. PATENT DOCUMENTS

| | | | |
|---|---|---|---|
| 2,719,688 A * | 10/1955 | Seifert | A47F 7/06 248/188.5 |
| 2,777,340 A | 1/1957 | Hettwer et al. | |
| 2,794,633 A * | 6/1957 | Delany | F15B 13/10 92/52 |
| 2,807,473 A | 9/1957 | Kiehne | |
| 2,957,353 A | 10/1960 | Babacz | |
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,021,920 A | 5/1977 | Kirschner et al. | |
| 4,162,399 A | 7/1979 | Hudson | |
| 4,247,216 A * | 1/1981 | Pansini | B25G 3/18 15/1.7 |
| 4,318,395 A * | 3/1982 | Tawara | G02B 23/2453 359/827 |
| 4,606,343 A * | 8/1986 | Conta | A61B 17/115 227/178.1 |
| 4,618,288 A * | 10/1986 | Daigle | E02D 9/00 405/228 |
| 4,692,073 A | 9/1987 | Martindell | |
| 4,693,389 A * | 9/1987 | Kalen | G21C 13/067 138/89 |
| 4,699,550 A * | 10/1987 | Baker | A61B 17/1695 408/139 |
| 4,705,038 A | 11/1987 | Sjostrom et al. | |
| 4,874,181 A | 10/1989 | Hsu | |
| 5,083,883 A * | 1/1992 | Ueda | B25G 3/26 403/316 |
| 5,104,025 A * | 4/1992 | Main | A61B 17/115 227/175.1 |
| 5,129,118 A | 7/1992 | Walmesley | |
| 5,129,570 A | 7/1992 | Schulze et al. | |
| 5,138,647 A * | 8/1992 | Nguyen | A61B 6/4225 378/189 |
| 5,152,744 A | 10/1992 | Krause et al. | |
| 5,222,956 A | 6/1993 | Waldron | |
| 5,255,993 A * | 10/1993 | Kovacs | F16B 7/042 403/316 |
| 5,312,023 A | 5/1994 | Green et al. | |
| 5,326,013 A | 7/1994 | Green et al. | |
| 5,330,480 A | 7/1994 | Meloul et al. | |
| 5,332,383 A * | 7/1994 | Hehl | B29C 45/17 425/190 |
| 5,347,988 A | 9/1994 | Hori | |
| 5,350,355 A | 9/1994 | Sklar | |
| 5,380,333 A | 1/1995 | Meloul et al. | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,413,267 A | 5/1995 | Solyntjes et al. | |
| 5,423,835 A * | 6/1995 | Green et al. | A61B 17/1285 227/901 |
| 5,449,365 A * | 9/1995 | Green | A61B 17/1285 227/901 |
| 5,467,911 A | 11/1995 | Tsuruta et al. | |
| 5,476,379 A | 12/1995 | Disel | |
| 5,487,499 A | 1/1996 | Sorrentino et al. | |
| 5,490,683 A | 2/1996 | Mickel et al. | |
| 5,505,737 A | 4/1996 | Gosselin et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,542,594 A | 8/1996 | McKean et al. | |
| 5,562,239 A | 10/1996 | Boiarski et al. | |
| 5,569,256 A | 10/1996 | Vaughn et al. | |
| 5,601,560 A | 2/1997 | Del Rio et al. | |
| 5,630,818 A | 5/1997 | Del Rio et al. | |
| 5,653,374 A | 8/1997 | Young et al. | |
| 5,667,517 A | 9/1997 | Hooven | |
| 5,704,534 A | 1/1998 | Huitema et al. | |
| 5,707,340 A * | 1/1998 | Hipp | A61B 1/00195 285/314 |
| 5,713,505 A | 2/1998 | Huitema | |
| 5,741,263 A | 4/1998 | Umber et al. | |
| 5,779,130 A | 7/1998 | Alesi et al. | |
| 5,779,404 A | 7/1998 | Jore | |
| 5,782,397 A | 7/1998 | Koukline | |
| 5,782,749 A * | 7/1998 | Riza | A61B 17/2909 600/117 |
| 5,782,836 A | 7/1998 | Umber et al. | |
| 5,820,009 A | 10/1998 | Melling et al. | |
| 5,833,704 A | 11/1998 | McCombs et al. | |
| 5,863,159 A | 1/1999 | Lasko | |
| 5,865,361 A * | 2/1999 | Milliman | A61B 17/07207 227/176.1 |
| 5,888,200 A | 3/1999 | Walen | |
| 5,893,851 A | 4/1999 | Umber et al. | |
| 5,904,687 A | 5/1999 | Del Rio et al. | |
| 5,908,427 A | 6/1999 | McKean et al. | |
| 5,928,238 A | 7/1999 | Scarborough et al. | |
| 5,928,241 A | 7/1999 | Menut et al. | |
| 5,941,891 A | 8/1999 | Walen | |
| 5,954,259 A | 9/1999 | Viola et al. | |
| 5,964,774 A | 10/1999 | McKean et al. | |
| 5,989,257 A | 11/1999 | Tidwell et al. | |
| 5,993,453 A * | 11/1999 | Bullara | A61B 17/16 606/79 |
| 5,993,454 A | 11/1999 | Longo | |
| 6,017,354 A | 1/2000 | Culp et al. | |
| 6,033,408 A | 3/2000 | Gage et al. | |
| 6,045,560 A | 4/2000 | McKean et al. | |
| 6,062,575 A | 5/2000 | Mickel et al. | |
| 6,079,894 A * | 6/2000 | Obitts | A61H 3/02 135/75 |
| 6,090,123 A | 7/2000 | Culp et al. | |
| 6,129,547 A | 10/2000 | Cise et al. | |
| 6,209,886 B1 | 4/2001 | Estes et al. | |
| 6,264,087 B1 | 7/2001 | Whitman | |
| 6,270,087 B1 | 8/2001 | Mickel et al. | |
| RE37,358 E | 9/2001 | Del Rio et al. | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,514,001 B1 | 2/2003 | Yezersky et al. | |
| 6,533,157 B1 | 3/2003 | Whitman | |
| 6,537,280 B2 | 3/2003 | Dinger et al. | |
| 6,601,270 B2 * | 8/2003 | Eckhardt | E05B 3/00 16/412 |
| 6,610,066 B2 | 8/2003 | Dinger et al. | |
| 6,611,793 B1 | 8/2003 | Burnside et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,792,390 B1 | 9/2004 | Burnside et al. | |
| 6,817,508 B1 | 11/2004 | Racenet et al. | |

(56) References Cited

U.S. PATENT DOCUMENTS

| | | |
|---|---|---|
| 6,846,308 B2 | 1/2005 | Whitman et al. |
| 6,846,309 B2 | 1/2005 | Whitman et al. |
| 6,849,071 B2 | 2/2005 | Whitman et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 7,032,798 B2 | 4/2006 | Whitman et al. |
| 7,055,731 B2 | 6/2006 | Shelton, IV et al. |
| 7,077,856 B2 | 7/2006 | Whitman |
| 7,111,769 B2 | 9/2006 | Wales et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,226,460 B2 * | 6/2007 | Gibson ............. A61B 17/2909 606/180 |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,487,788 B2 | 2/2009 | Baker |
| 7,487,899 B2 | 2/2009 | Shelton, IV et al. |
| 7,513,899 B2 * | 4/2009 | Grim ................ A61B 17/1666 606/79 |
| 7,549,564 B2 | 6/2009 | Boudreaux |
| 7,568,603 B2 | 8/2009 | Shelton, IV et al. |
| 7,588,176 B2 * | 9/2009 | Timm .............. A61B 17/07207 227/176.1 |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,799,039 B2 | 9/2010 | Shelton, IV et al. |
| 7,802,712 B2 | 9/2010 | Milliman et al. |
| 7,845,537 B2 | 12/2010 | Shelton, IV et al. |
| 7,905,897 B2 | 3/2011 | Whitman et al. |
| 7,918,230 B2 | 4/2011 | Whitman et al. |
| 7,947,034 B2 | 5/2011 | Whitman |
| 7,951,071 B2 | 5/2011 | Whitman et al. |
| 7,963,433 B2 | 6/2011 | Whitman et al. |
| 7,967,178 B2 | 6/2011 | Scirica et al. |
| 7,992,758 B2 | 8/2011 | Whitman et al. |
| 8,016,855 B2 | 9/2011 | Whitman et al. |
| 8,020,743 B2 | 9/2011 | Shelton, IV |
| 8,157,151 B2 | 4/2012 | Ingmanson et al. |
| 8,186,555 B2 | 5/2012 | Shelton, IV et al. |
| 8,220,367 B2 | 7/2012 | Hsu |
| 8,241,322 B2 | 8/2012 | Whitman et al. |
| 8,292,888 B2 | 10/2012 | Whitman |
| 8,357,144 B2 | 1/2013 | Whitman et al. |
| 8,365,972 B2 | 2/2013 | Aranyi et al. |
| 8,372,057 B2 | 2/2013 | Cude et al. |
| 8,391,957 B2 | 3/2013 | Carlson et al. |
| 8,469,423 B1 * | 6/2013 | Crowley, Jr. ............ B25G 1/04 294/174 |
| 8,490,853 B2 | 7/2013 | Criscuolo et al. |
| 8,882,548 B2 * | 11/2014 | Siebens ................ H01R 4/5008 439/864 |
| 8,951,264 B2 * | 2/2015 | Saidha ............... A61B 17/7032 606/104 |
| 9,744,662 B1 * | 8/2017 | Henry ...................... B25G 1/04 |
| 9,757,129 B2 * | 9/2017 | Williams ......... A61B 17/07207 |
| 9,890,566 B1 * | 2/2018 | Davidson ............ E05B 65/0089 |
| 2004/0111012 A1 | 6/2004 | Whitman |
| 2005/0125009 A1 * | 6/2005 | Perry ................. A61B 17/2909 606/139 |
| 2005/0184125 A1 * | 8/2005 | Marczyk .......... A61B 17/07207 227/176.1 |
| 2006/0107982 A1 * | 5/2006 | Tsai ........................ A61H 3/02 135/72 |
| 2006/0142656 A1 | 6/2006 | Malackowski et al. |
| 2006/0226195 A1 * | 10/2006 | Scirica ............. A61B 17/07207 227/175.1 |
| 2007/0029363 A1 | 2/2007 | Popov |
| 2007/0031184 A1 * | 2/2007 | Baxstrom ............... F16B 7/042 403/109.3 |
| 2007/0084897 A1 | 4/2007 | Shelton et al. |
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029577 A1 * | 2/2008 | Shelton ................ A61B 17/068 227/176.1 |
| 2008/0035193 A1 * | 2/2008 | Baker ...................... A61H 3/02 135/82 |
| 2008/0058801 A1 | 3/2008 | Taylor et al. |
| 2008/0083807 A1 * | 4/2008 | Beardsley ........ A61B 17/07207 227/175.1 |
| 2008/0083808 A1 * | 4/2008 | Scirica ............. A61B 17/07207 227/175.1 |
| 2008/0083812 A1 * | 4/2008 | Scirica ............. A61B 17/07207 227/176.1 |
| 2008/0109012 A1 | 5/2008 | Falco et al. |
| 2008/0185419 A1 | 8/2008 | Smith et al. |
| 2008/0208195 A1 | 8/2008 | Shores et al. |
| 2008/0251561 A1 | 10/2008 | Eades et al. |
| 2008/0251570 A1 * | 10/2008 | Mastri .............. A61B 17/07207 227/175.1 |
| 2008/0255607 A1 | 10/2008 | Zemlok |
| 2008/0262654 A1 | 10/2008 | Omori et al. |
| 2008/0281336 A1 | 11/2008 | Zergiebel |
| 2009/0030283 A1 * | 1/2009 | Freystein ............ G02B 23/2476 600/182 |
| 2009/0090763 A1 | 4/2009 | Zemlok et al. |
| 2009/0099876 A1 | 4/2009 | Whitman |
| 2009/0101693 A1 * | 4/2009 | Taylor ................ A61B 17/0644 227/176.1 |
| 2009/0182193 A1 | 7/2009 | Whitman et al. |
| 2009/0206131 A1 * | 8/2009 | Weisenburgh, II .......................... A61B 17/07207 227/175.2 |
| 2009/0209990 A1 | 8/2009 | Yates et al. |
| 2010/0108852 A1 * | 5/2010 | Hardtke ................ F16L 3/2056 248/571 |
| 2010/0239362 A1 * | 9/2010 | Wareham ............... F16B 7/042 403/109.3 |
| 2010/0292716 A1 * | 11/2010 | Kasvikis ............... A61B 1/0014 606/151 |
| 2010/0324368 A1 * | 12/2010 | Mathieu ................. A61M 39/10 600/131 |
| 2011/0108605 A1 * | 5/2011 | Sapienza .......... A61B 17/07207 227/180.1 |
| 2011/0121049 A1 | 5/2011 | Malinouskas et al. |
| 2011/0142198 A1 * | 6/2011 | Cekov .................... A61B 6/14 378/38 |

(56) References Cited

U.S. PATENT DOCUMENTS

| | | | |
|---|---|---|---|
| 2011/0218522 A1 | 9/2011 | Whitman | |
| 2011/0253765 A1 | 10/2011 | Nicholas et al. | |
| 2011/0290855 A1* | 12/2011 | Moore | A61B 17/072 227/180.1 |
| 2012/0076577 A1* | 3/2012 | Yanagihara | A61B 1/00087 403/375 |
| 2012/0104071 A1 | 5/2012 | Bryant | |
| 2013/0078108 A1* | 3/2013 | McCloud | F04D 25/0606 416/244 R |
| 2013/0098965 A1 | 4/2013 | Kostrzewski et al. | |
| 2013/0221063 A1* | 8/2013 | Aronhalt | A61B 17/0682 227/176.1 |
| 2013/0245676 A1* | 9/2013 | Cappola | A61B 17/07207 606/213 |
| 2014/0001236 A1* | 1/2014 | Shelton, IV | A61B 17/07207 227/176.1 |
| 2014/0056670 A1* | 2/2014 | Gebhard | B21D 43/057 414/225.01 |
| 2014/0236174 A1* | 8/2014 | Williams | A61B 17/00234 606/130 |
| 2014/0249557 A1* | 9/2014 | Koch, Jr. | A61B 17/072 606/170 |
| 2014/0263568 A1* | 9/2014 | Williams | A61B 17/068 227/180.1 |
| 2014/0358129 A1* | 12/2014 | Zergiebel | A61B 17/28 606/1 |
| 2014/0374564 A1* | 12/2014 | Schroeder | B60P 7/0815 248/503 |
| 2015/0327919 A1* | 11/2015 | Clopp | A61B 18/1485 606/41 |
| 2016/0031382 A1* | 2/2016 | Chinn | B60P 7/0815 248/222.11 |
| 2016/0138631 A1* | 5/2016 | Kresge | F16D 1/112 403/376 |
| 2016/0206181 A1* | 7/2016 | Kiedrowski | A61B 1/00128 |

FOREIGN PATENT DOCUMENTS

| | | | |
|---|---|---|---|
| EP | 1736112 | A1 | 12/2006 |
| EP | 1769754 | A1 | 4/2007 |
| EP | 1813203 | A2 | 8/2007 |
| EP | 1943958 | A1 | 7/2008 |
| EP | 1943976 | A2 | 7/2008 |
| EP | 1952769 | A2 | 8/2008 |
| EP | 2027819 | A1 | 2/2009 |
| EP | 2055243 | A2 | 5/2009 |
| EP | 2098170 | A2 | 9/2009 |
| EP | 2100561 | A2 | 9/2009 |
| WO | 2000/072760 | A1 | 12/2000 |
| WO | 2000/072765 | A1 | 12/2000 |
| WO | 2003/026511 | A1 | 4/2003 |
| WO | 2003/077769 | A1 | 9/2003 |
| WO | 2004107989 | A1 | 12/2004 |
| WO | 2006/042210 | A2 | 4/2006 |
| WO | 2007026354 | A1 | 3/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |

OTHER PUBLICATIONS

Japanese Office Action dated Dec. 7, 2017, issued in JP Application No. 2014126291.
European Search Report dated Nov. 12, 2014 issued in European Appln. No. 14175923.
International Search Report corresponding to PCT/US2005/027266, completed May 30, 2008 and dated Jun. 18, 2008; (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Australian Examination Report dated Mar. 16, 2018, in AU Appln. No. 2014203328.

* cited by examiner

COUPLING MEMBER CONFIGURED FOR USE WITH SURGICAL DEVICES

CROSS-REFERENCE TO RELATED APPLICATIONS

The present application is a Continuation application which claims that benefit of and priority to U.S. patent application Ser. No. 13/936,289, filed on Jul. 8, 2013, the entire content of which is incorporated herein by reference.

BACKGROUND

Technical Field

The present disclosure relates to a coupling member for coupling an actuating device to a removable tool assembly. More specifically, the present disclosure relates to a coupling member including a locking assembly for securing a surgical actuating device to a disposable loading unit or reload of a surgical apparatus.

Description of Related Art

Surgical apparatus including a surgical actuating device and a disposable single use or multiple use loading unit or reload are known. Typically, during a surgical procedure, a reload, which may be in the form of a stapler, clip applier or the like, is connected to a surgical actuating device to perform a surgical procedure. After the surgical procedure is completed, the spent reload may be replaced with a fresh reload to facilitate performance of another surgical procedure.

During surgical procedures, it is imperative that the reload be securely fastened to the surgical actuating device in a manner to prevent separation of the reload from the surgical actuating device during actuation of the reload. It is also important that the reload be capable of attachment to and detachment from the surgical actuating device quickly.

SUMMARY

As can be appreciated, an electromechanical surgical device including a tool assembly that is easy to install and configured to lock when the electromechanical surgical device is fired may prove useful in the surgical arena.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

An aspect of the present disclosure provides a surgical apparatus. The surgical actuating device including a shaft having a distal end supporting a first coupling member. The first coupling member including one or more pairs of aperture. A reload includes a tool assembly. The reload includes a second coupling member including a locking assembly. The second coupling member including a pair of spring pins that are positioned to be received within the at least one pair of apertures. The spring pins being movable from an inward position to a radial outward position. The locking assembly including a lock plate that is moveable from a first position located between the spring pins to prevent movement of the spring pins from the radial outward position to the inward position to a second position spaced from the spring pins. In the radial outward position, the spring pins are received within the apertures of the first coupling member to secure the reload to the surgical actuating member and wherein when the lock plate is in the first position, the reload cannot be separated from the surgical actuating device. The surgical actuating device may be electromechanically actuated.

The second coupling member may include an axle for supporting one or more springs and the pair of spring pins. The spring(s) may be positioned between the pair of spring pins and configured to bias the pair of spring pins to the radial outward position. Each of the spring pins of the second coupling member may include a tapered outer peripheral edge. Contact between the tapered outer edges of the spring pins and an outer edge of the first coupling member cams the spring pins inwardly against the bias of the spring(s).

The lock plate may include one or more hinges that pivotably couple the lock plate to an internal surface of the tool assembly of the reload. The lock plate may include a clevis at a top portion thereof. The clevis may be configured to connect to a proximal end of a plunger of the locking assembly. The plunger may support a spring for biasing the lock plate into engagement with the pair of spring pins when a knife of a cartridge of the tool assembly is fired.

The first coupling member may include two or more pairs of apertures. Each of the pairs of apertures may be configured to engage the pair of spring pins. The two pairs of apertures may be oriented orthogonally in relation to one another.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
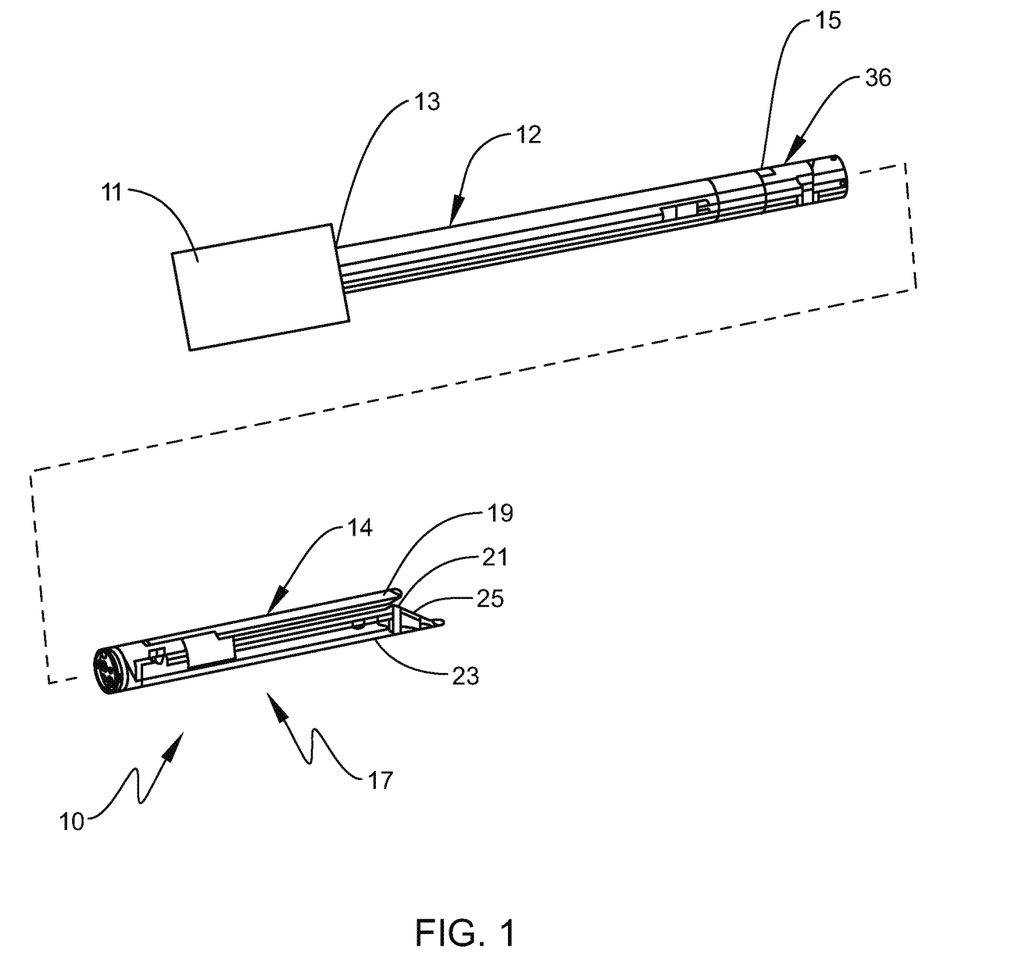
FIG. 1 is a perspective view of a reload, with parts separated, including a shaft including a first coupling member and an end effector member including a tool assembly including a second coupling member according to an embodiment of the instant disclosure.
Figure 2:
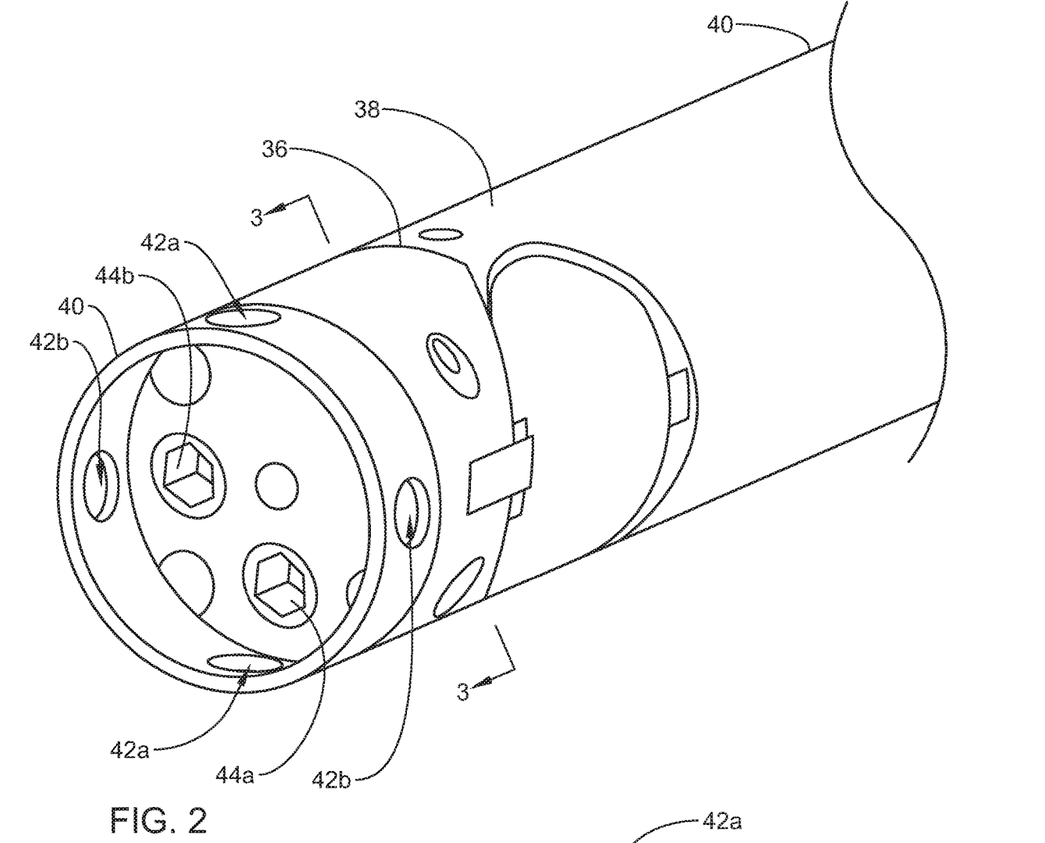
FIG. 2 is a perspective view of the first coupling member disposed at a distal end of the shaft of the reload shown in FIG. 1 according to an embodiment of the instant disclosure.
Figure 3:
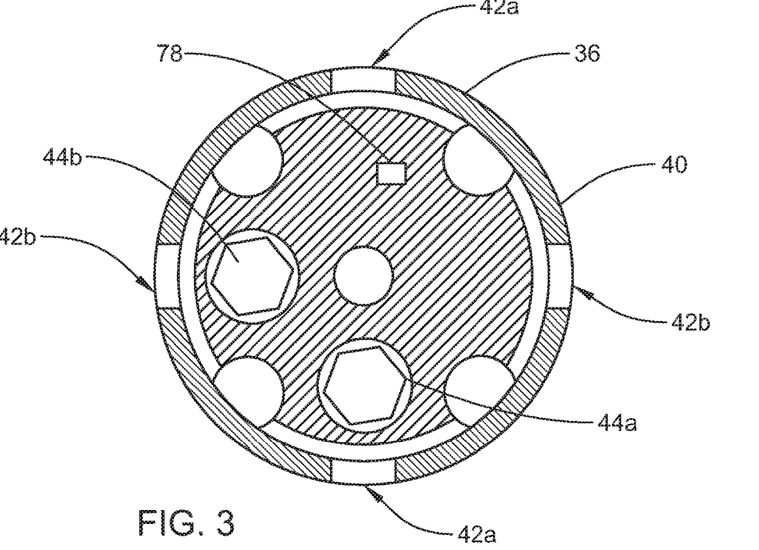
FIG. 3 is a cross sectional view taken along line segment 3-3 in FIG. 2.

Referring initially to FIG. 1, a reload 10 in accordance with the present disclosure is shown. Reload 10 may be configured to be coupled to a variety of different surgical actuating devices, shown schematically as 11 in FIG. 1, including manually operated actuation devices, robotically controlled actuation devices, electromechanical actuation devices, motorized actuation devices, etc. The reload 10 supports an end effector or tool assembly 14 which can be in the form of a stapler, clip applier, grasper or the like.

The surgical actuating device 11 includes a shaft assembly 12 which includes a distal end supporting a first coupling member 36 configured to releasably support the reload 10. In one embodiment, the tool assembly 14 is in the form of a stapler and includes a first jaw member 19 supporting an anvil 21 and a second jaw member 23 supporting a cartridge 25. In any of the embodiments disclosed herein, the cartridge 25 may be removably couplable to the second jaw member 23.

Referring to FIGS. 1-5, the first coupling member 36 is supported at the distal end 15 of the shaft assembly 12 and is configured to be removably coupled to a second coupling member 51 (FIG. 5) of the of the reload 10 to releasably couple the reload 10 to the surgical actuating device 11. The first coupling member 36 includes a collar 40 which includes two pairs of spaced apart apertures 42a, 42b that are oriented orthogonally with respect to one another. The apertures 42a, 42b are arranged to allow a user to couple the reload 10 to the shaft assembly 12 in at least two different positions relative to the distal end 15 of the shaft assembly 12. In embodiments, the apertures 42a, 42b may be tapered, beveled for reasons to be discussed in further detail below.

As noted above, the reload 10 may be configured for use with various surgical instruments. For example, in an embodiment, the reload may be configured for use with a surgical instrument that utilizes electromechanical linear driven actuation. In this particular embodiment, a pair of output drives 44a, 44b may be provided within the coupling member 36 and may be oriented 90 degrees from one another to engage the reload 10 when the reload 10 is coupled to the coupling member 36. The output drives 44a, 44b may be spaced 90 degrees from one another to give a clinician the flexibility to position the rotatably secure the reload 10 to the shaft assembly 12 by rotating the reload 10 in either a clockwise or counter clockwise direction in relation to the shaft assembly 12 as will be discussed in further detail below. In any of the embodiments disclosed herein, the apertures 42a and 42b can be spaced a different angular distance from one another, and the output drives arranged accordingly, so as to provide the surgeon with different orientation of the tool assembly with respect to the shaft of the instrument.

Figure 4:
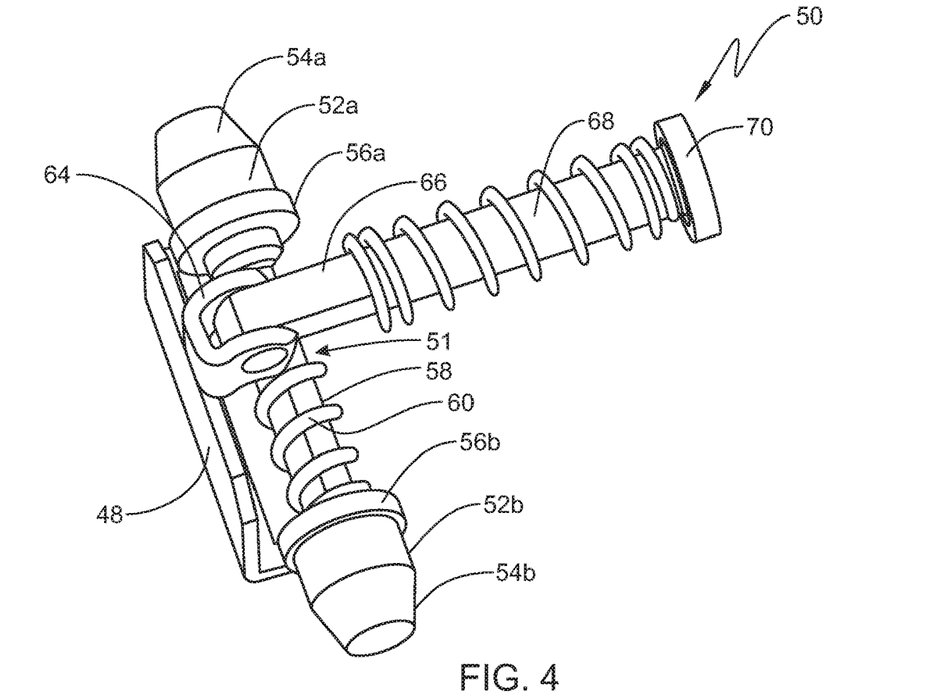
FIG. 4 is a perspective view of a locking assembly and a second coupling member including a pair of spring pins of the end effector shown in FIG. 1.
Figure 5:
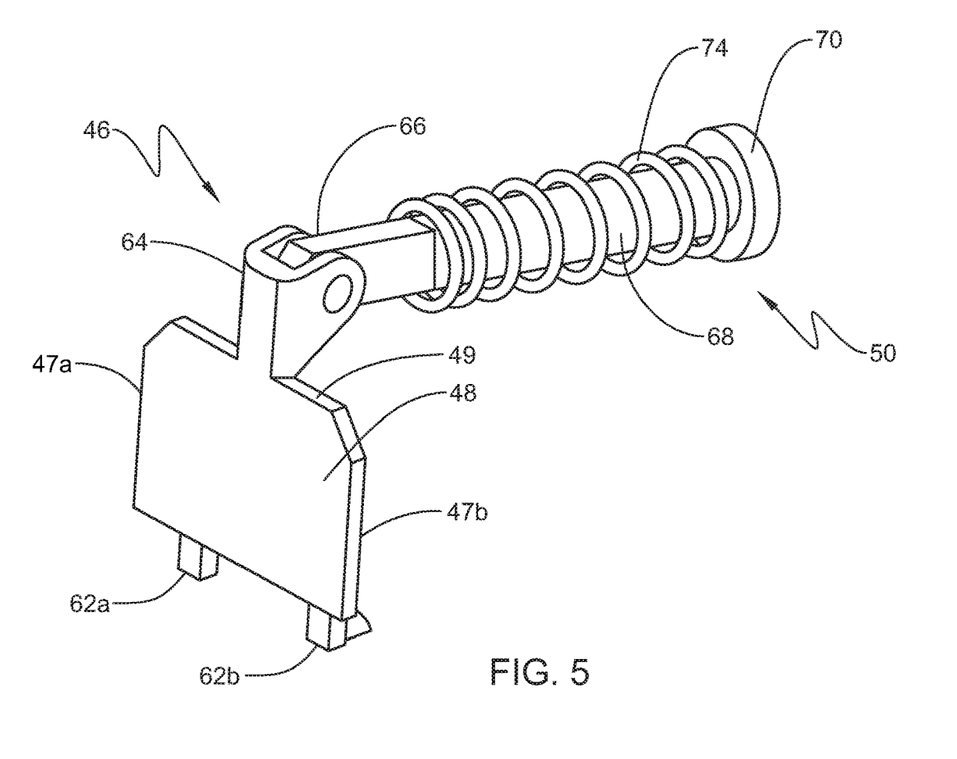
FIG. 5 is a perspective view of a lock plate and plunger of the locking assembly shown in FIG. 4.

Referring to FIGS. 4-5, the reload 10 includes a second coupling member 51. Coupling member 51 includes a pair of spring pins 52a, 52b which are configured to be received within a respective one of the pairs of apertures 42a or 42b defined in the first coupling member 36 for removably coupling the reload 10 to the distal end 15 of the shaft assembly 12. Each of the spring pins 52a, 52b can have a tapered outer peripheral edge 54a, 54b and an annular flange 56a, 56b. The pair of spring pins 52a, 52b is positioned on an axle 58. A biasing member, e.g., a spring 60, is positioned about each axle 58 and includes a first end which abuts a respective annular flange 56a, 56b and a second end which abuts a clevis 64 (FIG. 7) to bias the pair of spring pins 52a, 52b radially outwardly for reception within apertures 42a, 42b of first coupling member 36. The spring pins 52a, 52b are deflectable inwardly against the bias of the spring 60 when the proximal end of reload 10 is inserted into the first coupling member 36. More specifically, when the reload 10 is inserted into the first coupling member 36, the tapered edges 54a, 54b of pins 52a, 52b engage an outer wall of the first coupling member 36 and are cammed inwardly to allow passage of the second coupling member 51 into the first coupling member 36. Prior to positioning the second coupling member 51 within the first coupling member 36, the reload 10 may be rotated in relation to the shaft assembly 12 to align pins 52a, 52b with one of the pair of apertures 42a, 42b defined in the first coupling member 36 such that pins 52a, 52b are received within a respective pair of apertures 42a, 42b. As noted above, the apertures 42a, 42b may tapered, beveled or otherwise configured to guide the spring pins 52a, 52b into one of the corresponding pairs of apertures 42a, 42b on the first coupling member 36.

Figure 6:
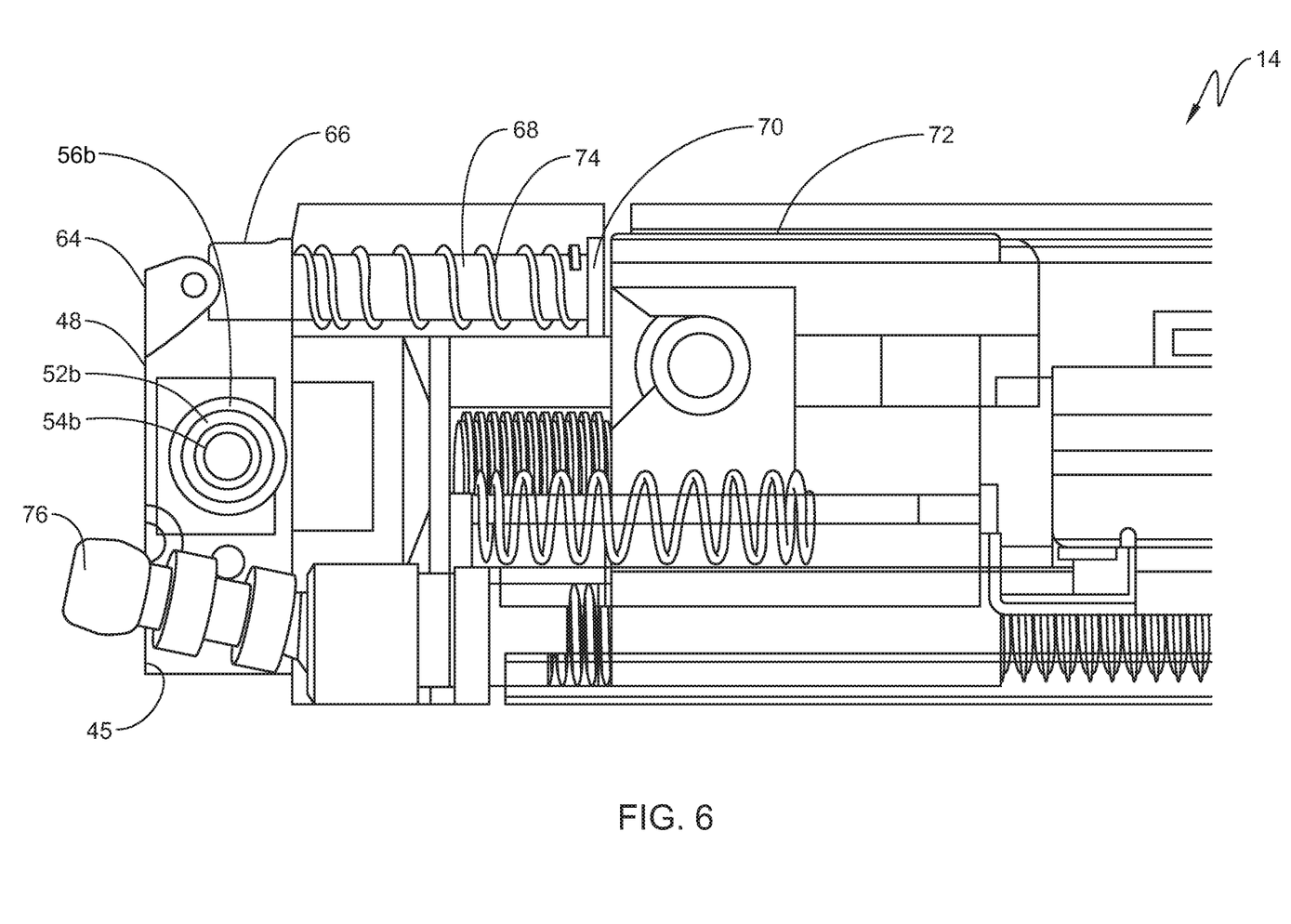
FIG. 6 is a partial, side view of the end effector shown in FIG. 1.

Referring to FIGS. 4-7, the second coupling member 51 also includes a lock assembly which includes a lock plate 48 and a plunger 50. The lock plate 48 includes a pair of left and right hinges 62a, 62b that are pivotably coupled to an internal surface 45 of the tool assembly 14 (as best seen in FIG. 6). Alternatively, a single hinge, living hinge or any structure capable of pivotally supporting the lock plate 48 adjacent the proximal end of the reload 10 may be provided to pivotally support the lock plate 10. In the illustrated embodiment, the lock plate 48 is pivotable about the hinges 62a, 62b from a first unlocked position (FIG. 7) to a second locked position (FIGS. 6 and 8). In the locked position, left and right sidewalls 47a, 47b of the lock plate 48 are positioned between the annular flanges 56a, 56b of spring pins 52a, 52b of the second coupling member 51. In this position, lock plate 48 prevents the spring pins 52a, 52b from moving radially inward and, thus, prevents pins 52a, 52b from exiting the apertures 42a, 42b to prevent separation of the reload 10 from the shaft assembly 12. In the unlocked position, the left and right sidewalls 47a, 47b of the lock plate 48 are not positioned between the annular flanges 56a, 56b of the spring pins 52a, 52b of the second coupling member 51. In this position, the spring pins 52a, 52b are capable of inward movement. A clevis 64 is provided at a top portion 49 of the lock plate 48 and is configured to connect to a proximal end 66 of the plunger 50 to the lock plate 48. The clevis 64 may be connected to the proximal end 66 of the plunger 50 via a pin, detent/indent configuration or other suitable connection method.

The plunger 50 includes an elongated body portion 68 that supports a flange 70 at a distal end thereof. The flange 70 is configured to contact a proximal end of a knife 72 (or clamping member) when the knife 72 is disposed in a proximal most position (see FIG. 7 for example). For a more detailed discussion of the knife 72 and other components of the reload (or loading unit), see U.S. Pat. No. 5,865,361 ('361 patent) which is incorporated herein by reference. A spring 74 is supported about the elongated body portion 68 of the plunger 50 between the flange 70 and an inner wall 70a (FIG. 8) of the reload housing 10a to urge the plunger 68 distally such that flange 70 abuts the knife 72. By biasing plunger 68 distally, lock plate 48 is urged towards the locked position (FIG. 8) between the spring pins 52a, 52b. When the knife 72 is in its proximal-most position, lock plate 48 is prevented from moving to the locked position. As such, when the knife 72 is in its proximal-most position, the reload 10 can be disengaged from the shaft assembly 12 of the surgical actuating device 11.

Figure 7:
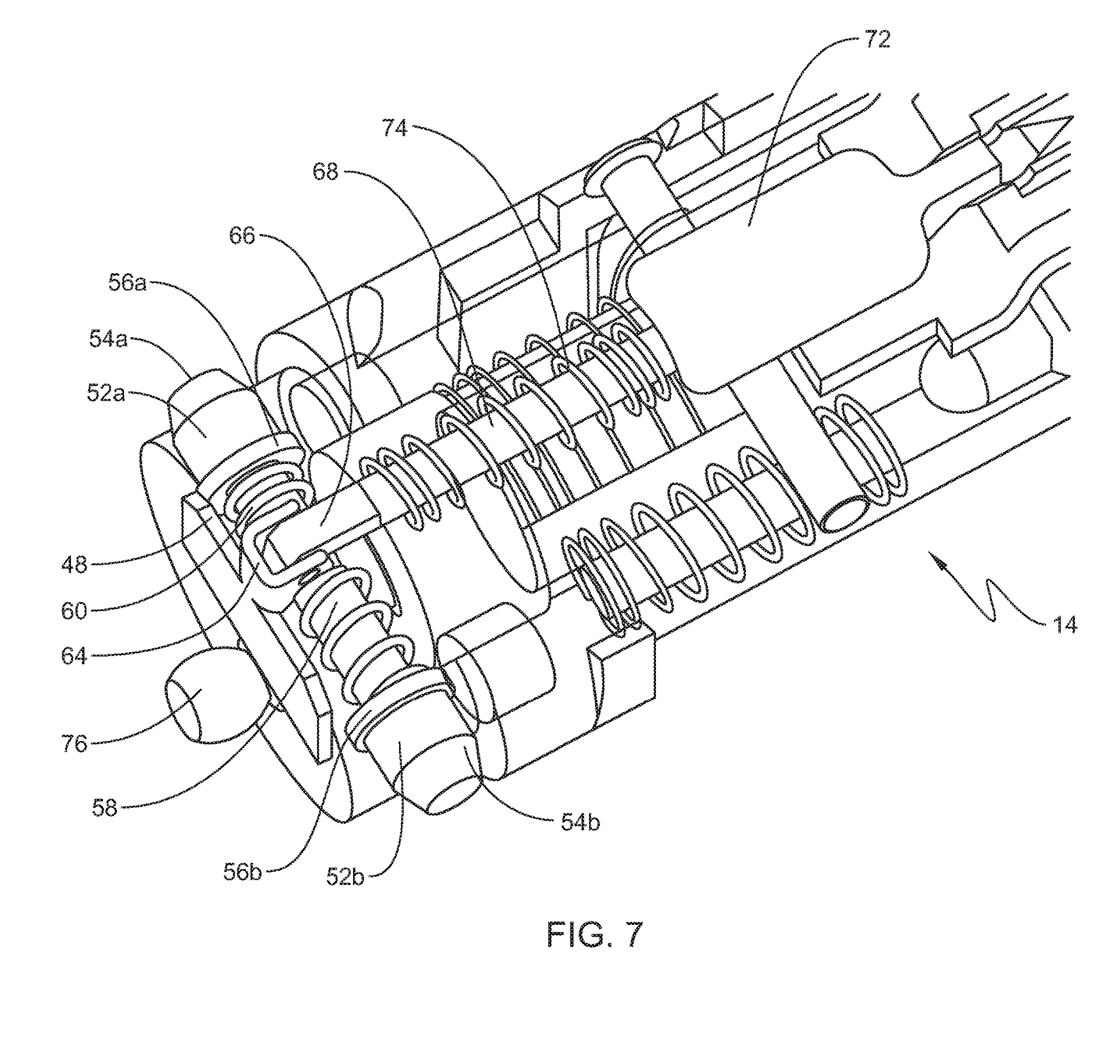
FIG. 7 is a partial, perspective view of the end effector, with an anvil of the tool assembly removed, to illustrate the lock plate and plunger shown in FIG. 5 in an unlocked configuration.
Figure 8:
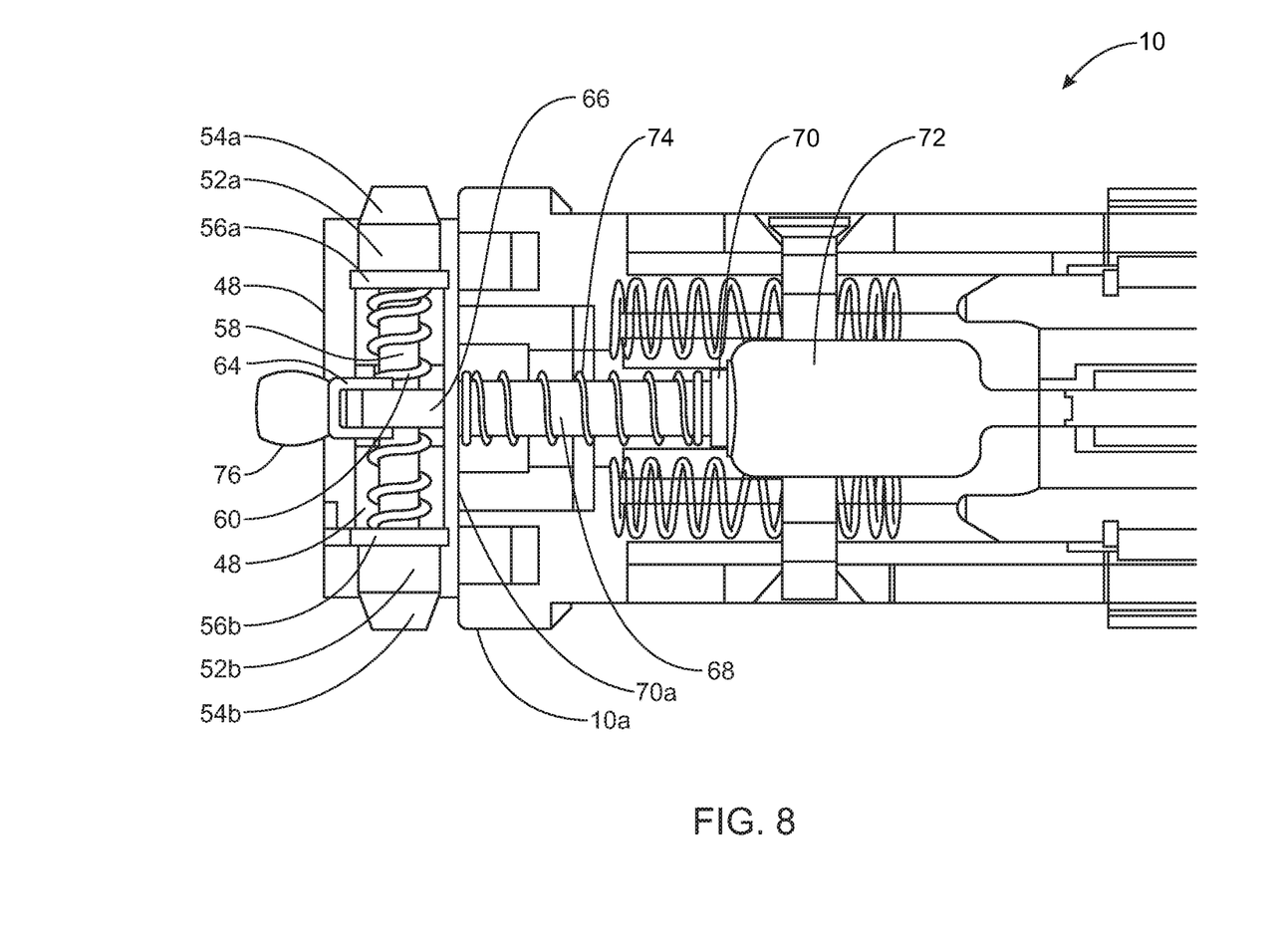
FIG. 8 is a top elevational view of the tool assembly shown in FIG. 7 with an anvil of the tool assembly removed, to illustrate the lock plate and plunger in a locked configuration.

Referring to FIGS. 6-7, as noted above, the surgical actuating device can include an electromechanical linear driven actuation. To this end, the reload 10 can include an input drive 76 at a proximal end of the tool assembly 14 which is configured to selectively engage either one of the output drives 44a, 44b included at the distal end of shaft assembly 12 adjacent the first coupling member 36. In the illustrated embodiment, the input drive 76 includes a hexagonal fitting that is received within a hexagonal recess of the output drives 44a, 44b. The input drive 76 can be connected to either of the output drives 44a, 44b depending on the orientation of the reload 10 in relation to the shaft assembly 12.

Figure 9:
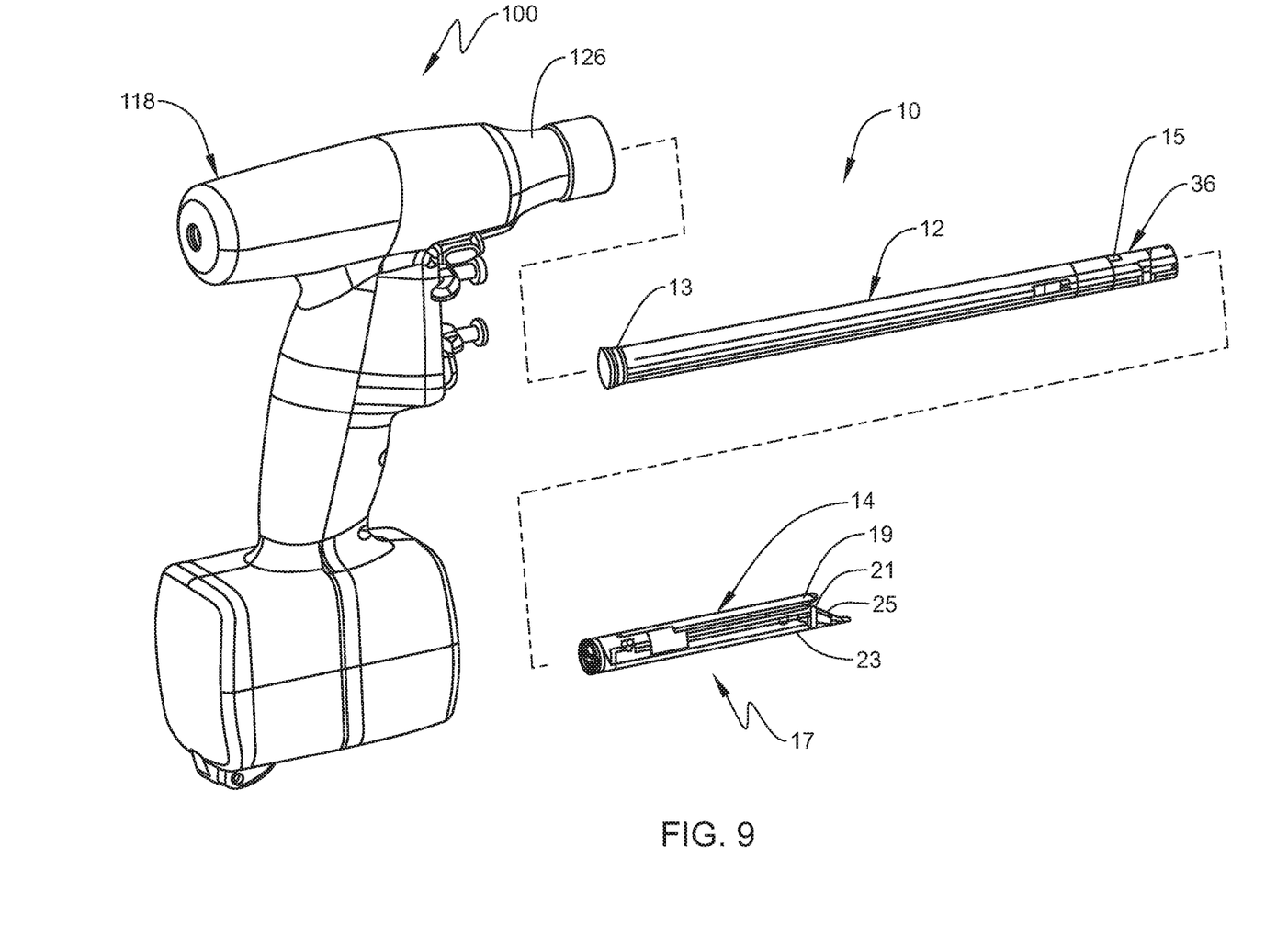
FIG. 9 is a perspective view of a powered surgical instrument configured for use with the reload shown in FIG. 1.

For illustrative purposes, operation of the reload 10 is now described in association with an electromechanical, handheld surgical stapling apparatus 100 (apparatus 100) shown in FIG. 9. It is noted that the coupling member 51 of reload 10 can be used to couple reload 10 to a variety of different surgical actuating devices 11 as discussed above.

Briefly, apparatus 100 includes a handle 118 that defines a nose or connecting portion 126 configured to releasably engage the proximal end 13 of the shaft assembly 12. Alternatively, the handle 118 and the shaft assembly 12 can be fixedly connected. A drive mechanism (not shown) is configured to drive the output drives 44a, 44b of shaft assembly 12 to actuate the tool assembly 14 to effect movement of anvil 19 and/or to fire the staples and sever tissue. This operation is described in detail in U.S. patent application Ser. Nos. 12/622,827, 13/769,419 which are incorporated herein by reference. In any of the embodiments disclosed herein, the shaft assembly can be removable and replaceable and can correspond to the particular reload being used (such as clip applier, electrosurgical, stapler configurations, etc.) or the shaft assembly can be permanently attached to the handle.

In use, the knife 72 of the cartridge 23 is initially positioned at a proximal end of the cartridge 23. The cartridge 23 can be installed onto a jaw member of the tool assembly 14 (FIG. 7) or, in the alternative, can be fixedly supported on the jaw member of the reload 10. In this position, the plunger 50 of the locking assembly 46 is biased proximally, which, in turn, maintains the lock plate 48 in the unlocked configuration, i.e., the lock plate 48 is positioned proximally of annular flanges 56a, 56b of the spring pins 52a, 52b such that inward movement of the spring pins 52a, 52b is permitted. In this configuration, a proximal end of the tool assembly 14 can be inserted into the first coupling member 36 so that the spring pins 52a, 52b of the second coupling member 51 are received within the pair of apertures 42a, 42b on the first coupling member 36. As can be appreciated, engagement of the tapered peripheral edges 54a, 54b of the spring pins 52a, 52b with the outer edge of the first coupling member 36 cams the spring pins 52a, 52b inwardly against the bias of the spring 60. This allows the first coupling member 36 to move into the second coupling member 51 to move the spring pins 52a, 52b of the second coupling member 51 into the apertures 42a, 42b of the first coupling member 36 to secure the reload 10 to the shaft assembly 12.

When the apparatus 100 is fired to staple tissue, the knife 72 moves out of engagement with the flange 70. When this occurs, the spring 74 urges the plunger 50 distally such that the lock plate 48 of the locking assembly 46 pivots about the hinges 62a, 62b and moves between the inside flange portions 56a, 56b of the spring pins 52a, 52b (FIGS. 6 and 8). In this configuration, the spring pins 52a, 52b are prevented from inward movement. Thus, spring pins 52a, 52b cannot be removed from apertures 42a, 42b and reload 10 cannot be disengaged from the shaft assembly 12.

Thereafter, the knife 72 may be returned to the proximal most position, which, in turn, moves the lock plate 48 proximally from between the spring pins 52a, 52b and out of the locked configuration. In this position, a user can remove the tool assembly 17 from the first coupling member. As noted above, the tapered peripheral edges 54a, 54b of the spring pins 52a, 52b facilitate biasing the spring pins 52a, 52b inwardly against the bias of the spring 60 as the spring pins 52a, 52b are moved into and out of engagement with the apertures 42a, 42b, which, in turn, allows the spring pins 52a, 52b to slide out of engagement with the apertures 42a, 42b with a simple axial motion.

The unique configuration of the locking assembly 46 and spring pins 52a, 52b overcome the aforementioned drawbacks, typically, associated with conventional staplers that are configured for use with removably couplable tool assemblies. That is, the tool assembly 14 is maintained in a locked configuration on at the distal end 15 of the shaft assembly 12 when the apparatus 100 is fired, and the tool assembly 14 can be installed to the first coupling member 36 with a simple straight push/pull motion.

From the foregoing and with reference to the various figure drawings, those skilled in the art will appreciate that certain modifications can also be made to the present disclosure without departing from the scope of the same. For example, one or more sensors 78 (FIG. 4) may be provided in and/or on the first coupling member 36 to detect when the tool assembly 14 is coupled to the first coupling member 36. In this embodiment, the sensor 78 may communicate with one or more components associated with any of the aforementioned surgical devices.

Moreover, the first coupling member 36 of the reload 10 may be modified to receive different linear drive mechanisms. For example, in an embodiment, the reload 19 may be configured to connect to a manually actuatable surgical stapling device that utilizes a drive beam configured to translate within a staple cartridge to fire a sled of the staple cartridge. In this embodiment, for example, the first coupling member 36 may include an aperture, slot or channel configured to receive the drive beam therethrough when the manually actuatable surgical stapling device is fired.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A reload comprising:
   a tool assembly and a coupling member, the coupling member including a locking assembly and spring pins, each of the spring pins being movable from an inward position to a radial outward position, the locking assembly including a lock plate having one end pivotably coupled to the tool assembly, the lock plate being moveable from a first position located between the spring pins to prevent movement of the spring pins from the radial outward position to the inward position to a second position spaced from the spring pins.

2. The reload of claim 1, wherein the coupling member includes an axle for supporting at least one spring and the spring pins, the at least one spring being positioned between the spring pins and configured to bias each of the spring pins to the radial outward position.

3. The reload of claim 1, wherein each of the spring pins of the coupling member includes a tapered outer peripheral edge.

4. A reload comprising:
a tool assembly and a coupling member, the coupling member including a locking assembly and spring pins, each of the spring pins being movable from an inward position to a radial outward position, the locking assembly including a lock plate that is moveable from a first position located between the spring pins to prevent movement of the spring pins from the radial outward position to the inward position to a second position spaced from the spring pins, wherein the lock plate includes at least one hinge that pivotably couples the lock plate to an internal surface of the tool assembly of the reload.

5. A reload comprising:
a tool assembly and a coupling member, the coupling member including a locking assembly and spring pins, each of the spring pins being movable from an inward position to a radial outward position, the locking assembly including a lock plate that is from a first position located between the spring pins to prevent movement of the spring pins from the radial outward position to the inward position to a second position spaced from the spring pins, wherein the one end of the lock plate includes a top portion that supports a clevis.

6. The reload of claim 5, wherein the locking assembly includes a plunger, and the clevis is configured to connect to a proximal end of the plunger.

7. A reload comprising:
a tool assembly and a coupling member including a locking assembly, the locking assembly including a plunger, the coupling member including a pair of spring pins, the pair of spring pins being movable from an inward position to a radial outward position, the locking assembly including a lock plate that is moveable from a first position located between the pair of spring pins to prevent movement of each of the pair of spring pins from the radial outward position to the inward position to a second position spaced from the spring pins, the lock plate having a top portion supporting a clevis, the clevis being configured to connect to a proximal end of the plunger of the locking assembly, and wherein the plunger supports a spring for biasing the lock plate into engagement with the pair of spring pins.

8. The reload of claim 7, wherein the coupling member includes an axle for supporting at least one spring and the pair of spring pins, the at least one spring being positioned between the pair of spring pins and configured to bias the pair of spring pins to the radial outward position.

9. The reload of claim 7, wherein each of the pair of spring pins of the coupling member includes a tapered outer peripheral edge.

10. The reload of claim 7, wherein the lock plate includes at least one hinge that pivotably couples the lock plate to an internal surface of the tool assembly of the reload.

* * * * *